(12) United States Patent
Jiang et al.

(10) Patent No.: US 11,739,357 B2
(45) Date of Patent: Aug. 29, 2023

(54) RECOMBINANT MICROORGANISM FOR PRODUCING CITICOLINE AND METHOD FOR PRODUCING CITICOLINE

(71) Applicant: SUZHOU BIOSYNTHETICA CO., LTD, Jiangsu (CN)

(72) Inventors: Junjun Jiang, Jiangsu (CN); Junying Fan, Jiangsu (CN); Feng Tian, Jiangsu (CN); Xintong Wang, Jiangsu (CN); Kailin Zhang, Jiangsu (CN); Zhihao Hu, Castro Valley, CA (US)

(73) Assignee: SUZHOU BIOSYNTHETICA CO., LTD, Suzhou (CN)

( * ) Notice: Subject to any disclaimer, the term of this patent is extended or adjusted under 35 U.S.C. 154(b) by 546 days.

(21) Appl. No.: 16/736,781

(22) Filed: Jan. 7, 2020

(65) Prior Publication Data

US 2020/0140910 A1    May 7, 2020

Related U.S. Application Data

(63) Continuation of application No. PCT/CN2018/075238, filed on Feb. 5, 2018.

(30) Foreign Application Priority Data

Jul. 7, 2017    (CN) .......................... 201710549120.0

(51) Int. Cl.
| | | |
|---|---|---|
| C12P 19/30 | (2006.01) | |
| C12N 1/20 | (2006.01) | |
| C12N 9/12 | (2006.01) | |
| C12N 15/70 | (2006.01) | |

(52) U.S. Cl.
CPC .............. *C12P 19/305* (2013.01); *C12N 1/20* (2013.01); *C12N 9/1205* (2013.01); *C12N 9/1241* (2013.01); *C12N 15/70* (2013.01); *C12Y 207/01032* (2013.01); *C12Y 207/07015* (2013.01)

(58) Field of Classification Search
CPC .......... C12P 19/305; C12P 19/30; C12N 1/20; C12N 9/1205; C12N 9/1241; C12N 15/70; C12N 9/14; C12N 15/52; C12N 9/16; C12N 9/93; C12Y 207/01032; C12Y 207/07015; C12Y 101/99001; C12Y 301/03001; C12Y 301/03005; C12Y 306/01026; C12Y 207/04022; C12Y 603/04016; C07K 14/245
See application file for complete search history.

(56) References Cited

U.S. PATENT DOCUMENTS

| | | | |
|---|---|---|---|
| 2013/0029395 A1 | 1/2013 | Schirmer et al. | |
| 2018/0230441 A1* | 8/2018 | Fukui | .................. C12P 7/24 |
| 2020/0140910 A1* | 5/2020 | Jiang | ............. C12Y 207/01032 |

FOREIGN PATENT DOCUMENTS

| | | |
|---|---|---|
| CN | 104774799 A | 7/2015 |
| CN | 106754602 A † | 5/2017 |
| EP | 1 669 461 A1 † | 6/2006 |
| JP | 5112869 B2 † | 1/2013 |
| WO | 2017/073701 A2 † | 5/2017 |

OTHER PUBLICATIONS

International Search Report of PCT Patent Application No. PCT/CN2018/075238 dated May 8, 2018.
Shoji Shirota et al., Effects of Pyrophosphate on Formation of Nucleotide Derivatives, Agricultural and Biological Chemistry, 1971, pp. 325-332, vol. 35, No. 3.
Isao Takata et al., Stabilization of Fumarase Activity of Brevibacterium flavum Cells by Immobilization with K-Carrageenan, Applied Biochemistry and Biotechnology, 1983, pp. 31-38, vol. 8.
Weiran Qiu et al., Study on Continuous Production of Cytodiphosphocholine Using Immobilized Cells, Chinese Journal of Biochemical Pharmaceutics, 1992, pp. 37-39, vol. 62, No. 4.
Dongsheng Yu et al., Biosynthesis of CDPC by Mixed Supports Immolibized Yeasts, Journal of Wuxi University of Light Industry, May 2002, pp. 277-280, vol. 21, No. 3.
Yuko Tsukagoshi et al., Expression in *Escherichia coli* of the *Saccharomyces cerevisiae* CCT Gene Encoding Cholinephosphate Cytidylyltransferase, Journal of Bacteriology, Mar. 1991, pp. 2134-2136, vol. 173, No. 6.
James R. Carter et al., Enzymatic synthesis of cytidine diphosphate diglyceride, Journal of Lipid Research, 1966, pp. 678-683, vol. 7, No. 5.
Emma Visedo Gonzalez et al., 2-Aminoethylarsonic acid as an analogue of ethanolamine phosphate, Biochem J, 1989, pp. 299-301, vol. 260, No. 1.
Felix Rohdich et al., Cytidine 5'-triphosphate-dependent biosynthesis of isoprenoids: YgbP protein of *Escherichia coli* catalyzes the formation of 4-diphosphocytidyl-2-C-methylerythritol, PNAS, Oct. 12, 1999, pp. 11758-11763, vol. 96, No. 21.
Meina Neumann et al., MocA Is a Specific Cytidylyltransferase Involved in Molybdopterin Cytosine Dinucleotide Biosynthesis in *Escherichia coli*, The Journal of Biological Chemistry, Aug. 14, 2009, pp. 21891-21898, vol. 284, No. 33.
Mohammad Ali Ghalambor et al., The Biosynthesis of Cell Wall Lipopolysaccharide in *Escherichia coli*, The Journal of Biological Chemistry, 1966, pp. 3216-3221, vol. 241, No. 13.

(Continued)

*Primary Examiner* — Ganapathirama Raghu

(57) ABSTRACT

The present invention provides a recombinant microorganism for producing citicoline and a method for producing citicoline by using the recombinant microorganism, wherein genes for degradation and utilization of citicoline, choline, and phosphocholine are knocked out, In addition, a pyrimidine nucleoside synthesis pathway is genetically engineered to remove feedback inhibition to the synthesis pathway. A yield of more than 20 g/L of citicoline can be obtained with recombinant strains in a 5-liter fermenter by means of a biological fermentation method, achieving industrial mass production with low citicoline production costs and less pollution; therefore, the method is a simple, environmentally friendly and has a relatively high promotion and application value.

3 Claims, 1 Drawing Sheet

(56) References Cited

OTHER PUBLICATIONS

Pei-Yong Shi et al., CCA addition by tRNA nucleotidyltransferase: polymerization without translocation?, The EMBO Journal, 1998, pp. 3197-3206, vol. 17, No. 11.

Dalia Denapaite et al., The Genome of *Streptococcus mitis* B6—What Is a Commensal?, PLoS One, Feb. 2010, vol. 5, No. 2, e9426.

Meihui Chang et al., Improving the Thermostability of Acidic Pullulanase from Bacillus naganoensis by Rational Design, PLoS One, 2016, vol. 11, No. 10, e0165006.

Giovanni Gadda et al., Cloning, Expression, and Purification of Choline Dehydrogenase from the Moderate Halophile Halomonas elongata, Applied and Environmental Microbiology, Apr. 2003, pp. 2126-2132, vol. 69, No. 4.

Jonathan Wittenberg et al., Choline Phosphokinase, J. Biol. Chem, 1953, pp. 431-444, vol. 202.

Cheng-Po Sung et al., Phosphorylation of Choline and Ethanolamine in Ehrlich Ascites-Carcinoma Cells, Biochem. J., 1967, pp. 497-503, vol. 105.

Akshai Iyengar et al., Aspartate-107 and leucine-109 facilitate efficient coupling of glutamine hydrolysis to CTP synthesis by *Escherichia coli* CTP synthase, Biochem. J., 2003, pp. 497-507, vol. 369.

Neel Devroede et al., Mutational Analysis of Intervening Sequences Connecting the Binding Sites for Integration Host Factor, PepA, PurR, and RNA Polymerase in the Control Region of the *Escherichia coli* carAB Operon, Encoding Carbamoylphosphate Synthase, Journal of Bacteriology, May 2006, pp. 3236-3245, vol. 188, No. 9.

Jin-Sook Kim et al., Deoxycytidine production by a metabolically engineered *Escherichia coli* strain, Microb Cell Fact, 2015, 14:98.

Sylviane Delannay et al., Serine 948 and Threonine 1042 are Crucial Residues for Allosteric Regulation of *Escherichia coli* Carbamoylphosphate Synthetase and Illustrate Coupling Effects of Activation and Inhibition Pathways, J. Mol. Biol., 1999, pp. 1217-1228, vol. 286, No. 4.

Laëtitia Coudray et al., Synthesis and In Vitro Evaluation of Aspartate Transcarbamoylase Inhibitors, Bioorg Med Chem., Nov. 15, 2009, pp. 7680-7689, vol. 17, No. 22.

Kaj Frank Jensen, The *Escherichia coli* K-12 "Wild Types" W3110 and MG1655 Have an rph Frameshift Mutation That Leads to Pyrimidine Starvation Due to Low pyrE Expression Levels, Journal of Bacteriology, Jun. 1993, pp. 3401-3407, vol. 175, No. 11.

Megumi Shimaoka et al., Effect of Amplification of Desensitized purF and prs on Inosine Accumulation in *Escherichia coli*, Journal of Bioscience and Bioengineering, 2007, pp. 255-261, vol. 103, No. 3.

Philippe Meyer et al., Structural and Functional Characterization of *Escherichia coli* UMP Kinase in Complex with Its Allosteric Regulator GTP, The Journal of Biological Chemistry, Dec. 19, 2008, pp. 36011-36018, vol. 283, No. 51.

Kirill A. Datsenko et al., One-step inactivation of chromosomal genes in *Escherichia coli* K-12 using PCR products, Proc Natl Acad Sci, Jun. 6, 2000, pp. 6640-6645, vol. 97, No. 12.

J. M. Lord, Glycolate Oxidoreductase in *Escherichia coli*, Biochim Biophys Acta, 1972, pp. 227-237, vol. 267, No. 2.

Jurgen Brosius et al., Spacing of The -10 and -35 Regions in the Tag Promoter Effect on Its in Vivo Activity, the Journalof Biological Chemistry, 1985, pp. 3539-3541, vol. 260, No. 6.

Alfred Walz et al., Sequence of the PR promoter of phage λ, Nature, 1975, pp. 118-121, vol. 254.

Tomoya Baba et al., Construction of *Escherichia coli* K-12 in-frame, single-gene knockout mutants: the Keio collection. Molecular Systems Biology, 2006, vol. 2, No. 1.

J. Sambrook, Molecular Cloning: A Laboratory Manual, translated by Huang Peitang, 2002, 1595.

Alkaline Phosphatase, http://ecocyc.org/, (2020).

Bifunctional Choline Kinase/Ethanolamine Kinase, https://www.biocyc.org/gene?orgid=YEAST&id=YLR133W-MONOMER, (2019).

Bifunctional Choline Kinase/Ethanolamine Kinase, https://biocyc.org/gene?orgid=YEAST&id=YDR147W-MONOMER, (2019).

Kim et al., "Isolation and Characterization of the *Saccharomyces cerevisiae* EKI1 Gene Encoding Ethanolamine Kinase," J. Biol. Chem., 274(21): 14857-14866 (1999).†

Shen et al., "The CDS1 Gene Encoding Cdp-diacylglycerol Synthase in *Saccharomyces cerevisiae* Is Essential for Cell Growth," J. Biol. Chem., 271(2): 789-795 (1996).†

Kelley et al., "Purification and Characterization of CDP-Diacylglycerol Synthase from *Saccharomyces cerevisiae*," J. Biol. Chem., 262(30): 14563-14570 (1987).†

Rock et al., "The licC Gene of *Streptococcus pneumoniae* Encodes a CTP:Phosphocholine Cytidylyltransferase," J. Biol. Chem., 183(16): 4927-4931 (2001).†

Xie et al., "Phospholipase D activity is required for suppression of yeast phosphatidylinositol transfer protein defects," Proc. Natl. Acad. Sci. USA, 95: 12346-12351 (1998).†

Neumann et al., "MocA Is a Specific Cytidylyltransferase Involved in Molybdopterin Cytosine Dinucleotide Biosynthesis in *Escherichia coli*," J. Biol. Chem., 284(33): 21891-21898 (2009).†

Strohmaier et al., "Expression of Genes kdsA and kdsB Involved in 3-Deoxy-D-manno-Octulosonic Acid Metabolism and Biosynthesis of Enterobacterial Lipopolysaccharide Is Growth Phase Regulated Primarily at the Transcriptional level in *Escherichia coli* K-12," J. Bacteriology, 177(15): 4488-4500 (1995).†

Min-Seok et al., "Isolation and Characterization of ECT1 Gene Encoding CTP: Phosphoethanolamine Cytidylyltransferase of *Saccharomyces cerevisiae*," J. Biochem., 120: 1040-1047 (1996).†

Zhang et al., "A Second Target of the Antimalarial and Antibacterial Agent Fosmidomycin Revealed by Cellular Metabolic Profiling," Biochemistry, 50(17): 3570-3577 (2011).†

Tomari et al., "The role of tightly bound ATP in *Escherichia coli* tRNA nucleotidyltransferase," Genes to Cells, 5: 689-698 (2000).†

Thaller et al., "Identification of the gene (aphA) encoding the class B acid phosphatase/phosphotransferase of *Escherichia coli* MG1655 and characterization of its product," FEMS Microbiology Letters, 146: 191-198 (1997).†

Weiss, "YjjG, a dUMP Phosphatase, Is Critical for Thymine Utilization by *Escherichia coli* K 12," J. Bacteriology, 189(5): 2186-2189 (2007).†

GenBank, "CTP: phosphocholine cytidylyltransferase, putative [Candida dubliniensis CD36]," https://www.ncbi.nlm.nih.gov/protein/CAX41949.1 (Feb. 27, 2015).†

Reaves et al., "Pyrimidine homeostasis is accomplished by directed overflow metabolism," Nature, 500: 237-242 (2013).†

Kakehi et al., "Complete Deficiency of 5'-Nucleotidase Activity in *Escherichia coli* Leads to Loss of Growth on Purine Nucleotides but Not of Their Excretion," J. Mol. Microbiol. Biotechnol., 13: 96-104 (2007).†

Bulawa et al., "Isolation and Characterization of *Escherichia coli* Strains Defective in CDP diglyceride Hydrolase," J. Biol. Chem., 259(18): 11257-11264 (1984).†

Riley, "Functions of the Gene Products of *Escherichia coli*," Microbiological Reviews, 57(4): 862-952 (1993).†

Inouye et al., "Cloning and Restriction Mapping of the Alkaline Phosphatase Structural Gene (phoA) of *Escherichia coli* and Generation of Deletion Mutants In Vitro," J. Bacteriology, 146(2): 668-675 (1981).†

Amini et al., "An enzymatic flow analysis method for the determination of phosphatidylcholine in sediment pore waters and extracts," Talanta, 66: 445-452 (2005).†

Forleo et al., "Expression, purification, crystallization and preliminary X-ray characterization of the class B acid phosphatase (AphA) from *Escherichia coli*," Acta Cryst., D59: 1058-1060 (2003).†

Domenech et al., "Pseudomonas aeruginosa acid phosphatase: Activation by divalent cations and inhibition by aluminum ion," Federation Euro. Biochemical Societies, 299(1): 96-98 (1992).†

Liu et al., "Efficient multi-enzyme-catalyzed CDP-choline production driven by an ATP donor module," Applied Microbiological Biotechnology, 101: 1409-1417 (2017).†

Alves-Pereira et al., "CDP-Alcohol Hydrolase, a Very Efficient Activity of the 5'-Nucleotidase/UDP-Sugar Hydrolase Encoded by the ushA Gene of Yersinia intermedia and *Escherichia coli*," J. Bacteriology, 190(18): 6153-6161 (2008).†

(56) References Cited

OTHER PUBLICATIONS

Bulawa et al., "Chloroform-soluble Nucleotides in *Escherichia coli*: Role of CDP-Diglyceride in the Enzymatic Cytidylylation of Phosphomonoester Acceptors," J. Biol. Chem., 258(24): 14974-14980 (1983).†
Imperial et al., "Enzyme Kinetic Equations of Irreversible and Reversible Reactions in Metabolism," J. Biosciences & Medicines, 2014(2): 24-29 (2014).†
Andresen et al., "Molecular Cloning, Physical Mapping and Expression of the bet Genes Governing the Osmoregulatory Choline—Glycine Betaine Pathway of *Escherichia coli*," J. General Microbiology, 134: 1737-1746 (1988).†

\* cited by examiner
† cited by third party

RECOMBINANT MICROORGANISM FOR PRODUCING CITICOLINE AND METHOD FOR PRODUCING CITICOLINE

CROSS-REFERENCE TO PRIOR APPLICATION

This application is a continuation application of PCT application No. PCT/CN2018/075238 filed on Feb. 5, 2018, which claims the benefit of Chinese Patent Application No. 201710549120.0 filed on Jul. 7, 2017. The contents of the above applications are incorporated herein by reference.

TECHNICAL FIELD

The present invention belongs to the field of biotechnologies, and in particular, relates to a recombinant microorganism for producing citicoline, production of citicoline by using the recombinant microorganism, and production of citicoline by means of a biological method using the recombinant microorganism.

BACKGROUND ART

Citicoline (CDP-choline, CDPC for short) is a nucleoside derivative, which is synthesized from 5'-cytidine acid and phosphocholine, and has a molecular formula of $C_{14}H_{26}N_4O_{11}P_2$, a relative molecular weight of 488.323962, and a boiling point of 851.4° C. The citicoline is an intermediate in the generation of phosphatidylcholine from choline, which is present in all cells and is a main coenzyme for phospholipid synthesis. The citicoline improves brain functions by promoting the synthesis of lecithin, and is used for treating acute craniocerebral trauma and post-brain operation consciousness disturbance.

There are mainly two methods for producing citicoline: a chemical method and a biological method. In the chemical synthesis method, citicoline sodium is generated under the action of N-dimethylformamide by using cytidylic acid and phosphocholine as substrates and toluene sulfonyl chloride as a condensing agent. However, this method has a low reaction conversion rate, produces many by-products, requires high costs, and generates much pollution.

The biological method for producing citicoline has a relatively long history, and mainly includes a single-enzyme/multi-enzyme catalysis method or a single-bacterium/multi-bacterium conversion method. In 1975, Shoji Shirota et al. studied the synthesis of citicoline using yeast and influencing factors in the synthesis (Shoji 1975 1971, Agr Biol Chen, 35(3):325-332.). In 1982, Isao Takata et al. biosynthesized CDPC by using compound K2 carrageenan to immobilize Fumarase enzyme (Takata J 1983, Appl Biochem Biotechnol 8, 31-38.). From 1992 to 2002, Qiu Weiran et al. produced citicoline by using immobilized yeast cells (Qiu Weiran 1992, Chinese Journal of Biochemical Pharmaceutics, 62(4):37-39.; Yu Dongsheng 2002, Journal of Wuxi University of Light Industry, 21(3):277-280.). In recent years, use of yeasts, *Brevibacterium ammoniagenes*, or the like for producing citicoline by means of fermentation, with orotic acid and phosphocholine being used as substrates and glucose being added to produce ATP, still has the problems such as high costs and a low conversion rate (Ying Hanjie 2015, GENETICALLY ENGINEERED BACTERIUM STRAIN EXPRESSING CHOLINE KINASE AND PHOSPHOCHOLINE CYTIDYLYLTRANSFERASE AND CONSTRUCTION METHOD AND APPLICATION THEREOF, 201510184705.8), not conducive to large-scale industrial production and application.

Therefore, there is a need to develop a non-polluting and low-cost, simple citicoline synthesis method, by which the large-scale industrial production of citicoline can be effectively implemented, thereby reducing production costs of citicoline and reducing pollution.

At present, just in China, an annual demand for citicoline reaches 1,000 tons, while currently only about 50 tons of citicoline can be provided. The present invention satisfies the above requirements and has related advantages.

SUMMARY OF THE INVENTION

The objectives of the present invention is to design and produce a recombinant microorganism capable of producing, synthesizing, and accumulating a relatively large amount of citicoline, and to achieve high-yield biological production of citicoline by using the recombinant microorganism with choline chloride used as a substrate.

Technical Solutions

1. Removal of Encoding Genes of Enzymes that Utilize and Degrade Citicoline

First, the encoding genes of enzymes that utilize and degrade citicoline in a cell are knocked out or blocked, such that the microorganism can accumulate citicoline (CDPC). These enzymes comprise: cytidine-5'-diphosphate-diacylglycerol pyrophosphatase (Cdh), and UDP-sugar hydrolase (UshA), which may catalyze citicoline to generate cytosine and phosphocholine.

2. Synthesis of Citicoline from Cytidine Acylation of Phosphocholine

In natural organisms, there is cytidylyltransferase (EC2.7.7, collectively referred to as CTase) that can dephosphorylate cytidine triphosphate (CTP) and generate citicoline and pyrophosphate with phosphocholine (PC), for example, PCT1 (Tsukagoshi Y 1991, J Bacteriol. 173(6): 2134-6.), CDS1 (Carter 1966, J Lipid Res 7(5); 678-83.), and ECT1 (Visedo Gonzalez 1989, Biochem J 260(1); 299-301.) derived from *Saccharomyces cerevisiae*; CdsA (Carter 1966, J Lipid Res 7(5); 678-83.), IspD (Rohdich 1999, Proc Natl Acad Sci USA 1999; 96(21); 11758-63.), MocA (Neumann 2009, J Biol Chem 284(33); 21891-8.), KdsB (Ghalambor 1966, J Biol Chem 1966; 241(13); 3216-21.), and Cca (Shi 1998, EMBO J 17(11); 3197-206.) derived from *Escherichia coli*; LicC (Denapaite D 2010 PLoS One. 5(2):e9426.) derived from *Streptococcus mitis* B6; Pcyt1a (Gene ID: 13026) and Pcyt1b (Gene ID: 236899) derived from *Mus musculus*; PAS_chr2-2_0401 (Gene ID: 8199108) derived from *Komagataella phaffii* GS115; CD36_40620 derived from *Candida dubliniensis* CD36; Cct 1 (Gene ID: 117353) and Cct2 (Gene ID: 38180) derived from fruit flies, and the like.

Encoding genes of these CTases specific to CTP or/and homologous enzymes thereof can be obtained by means of a DNA synthesis method, or can be directly obtained by means of a PCR method with mRNA extracted from corresponding organisms being used as a template. Therefore, when any of the genes obtained above is expressed in a recombinant cell, successfully expressed CTase can produce CDPC with CTP and PC being used as substrates in the recombinant cell, significantly increasing the yield of CDPC.

In order to further obtain certain CTase with higher specificity, protein engineering techniques can be used to obtain a CTase mutant with high specificity to CTP, so as produce a great amount of CDPC in the recombinant cell (for example, protein engineering is used for improving the thermostability of pullulanase in *Bacillus* (Chang 2016, MPLoS One. 11(10):e0165006.)).

3. Enhancement of Choline and Phosphocholine Supply in a Cell

In order to obtain more phosphocholine, choline chloride needs to be supplied more quickly. In order to increase choline chloride pool in a cell, choline transporter protein BetT is expressed, so as to obtain more transporter protein.

Most wild-type organisms can produce a variety of phosphorylases, such as acid phosphorylase and alkaline phosphorylase. For example, *Escherichia coli* produces acid phosphorylase (AphA) and alkaline phosphorylase (PhoA). Intracellular phosphocholine is prone to be hydrolyzed into choline and phosphate by these phosphatases. Choline is further dehydrogenated to generate glycine betaine. Dehydrogenases capable of degrading choline comprise choline dehydrogenases BetA and BetB of *Escherichia coli* (Gadda 2003, Appl Environ Microbiol 69(4); 2126-32.) and glycolate oxidases GlcD, GlcE, and GlcF (Lord 1972, Biochim Biophys Acta 1972; 267(2); 227-37.).

As a precursor of CDPC, continuous supply of phosphocholine is very important. To this end, 1) the choline transporter protein is expressed or overexpressed in a recombinant cell to accelerate entering of choline into the cell; 2) the cell is necessarily deficient in phosphorylases to achieve sustained and stable supply of phosphocholine; and 3) choline kinase (CKase) is expressed or overexpressed in the recombinant cell, thereby accelerating phosphorylation of choline to generate phosphocholine. The related choline kinase may not be present in all non-genetically modified cells. Choline kinases currently known to be capable of catalyzing the phosphorylation of choline comprise CKI1 (Wittenberg 1953, J. Biol. Chem., 202: 431-444) and EKI1 (SUNG1967, Biochem. J. 105,497) derived from *Saccharomyces cerevisiae*; Chka (Gene ID: 12660) and Chkb (Gene ID: 12651) derived from *Mus musculus*; CHKA (Gene ID: 1119) and CHKB (Gene ID: 1120) derived from *Homo sapiens*; CK1 (Gene ID: 843500) derived from *Arabidopsis thaliana*; Cka-1 (Gene ID: 177807), Cka-2 (Gene ID: 180703), Ckb-1 (Gene ID: 181904), Ckb-2 (Gene ID: 175565), and Ckb-4 (Gene ID: 184864) derived from *Caenorhabditis elegans*, and the like. 3). Since in the present invention, a substrate (choline chloride) is added during fermentation, in order to prevent degradation of the substrate, an enzyme capable of degrading choline must be blocked or its coding gene to be knocked out.

4. Increase of the Concentration of a Precursor CTP of CDPC

Intracellular CTP is an intermediate product of a pyrimidine synthesis pathway and is generated from uridine triphosphate (UTP) under the action of the cytidine triphosphate synthetase PyrG. However, PyrG is subject to feedback inhibition of a product CDP thereof. Mutations from aspartic acid to glutamic acid (D160E) at position 160, from glutamic acid to alanine (E162A) at position 162, or from glutamic acid to lysine at position 168 (E168K) of said enzyme can effectively remove the feedback inhibition effect of CDP thereon (Iyengar A 2003, Biochem J. 369(Pt 3):497-507). Cytidine monophosphate (CMP) may be generated from CTP under the action of 5-hydroxy-CTP pyrophosphatase NudG. Knocking out or blocking an encoding gene of NudG can effectively prevent shunting of CTP to accumulate CTP to higher concentration, thereby increasing the yield of CDPC.

5. Blocking of Uridine Monophosphate UMP Hydrolysis Pathway

In a pyrimidine synthesis pathway of *Escherichia coli*, UMP, which is an intermediate product in citicoline synthesis, is not only used to synthesize citicoline from CTP, but also used to generate uridine under the catalysis of various 5'-nucleotidases. Blocking or knocking out umpG and umpH, which are known to encode genes of 5'-nucleotidases, can remove shunting of UMP, so that UMP is used exclusively for CDPC synthesis.

6. Removal of Feedback Inhibition and Feedback Repression on Pyrimidine Nucleoside Synthesis, and Increase of the Metabolic Flux of the Pyrimidine Nucleoside Synthesis and the Yield of CDPC A first step of catalysis in a pyrimidine nucleotide synthesis pathway is catalyzing synthesis of carbamoyl phosphate by carbamoyl phosphate synthetase (CarAB). Said enzyme is respectively subject to feedback repression imposed by metabolic end products such as purine, pyrimidine, and arginine (Devroede N 2006, J Bacteriol. 188(9): 3236-45.), and corresponding repressor proteins are respectively PurR, PepA, and ArgR (Kim 2015, Microb Cell Fact 14:98). In the present invention, transcription inhibition to carAB genes is removed by knocking out genes purR, pepA, and argR thereby accelerating the synthesis of carbamoyl phosphate. In addition, said enzyme is further subject to feedback inhibition imposed by UMP. According to a literature report (Delannay S 1999, J Mol Biol. 286(4):1217-28), a mutation from serine (which is an amino acid at position 948) to phenylalanine (S948F) of a subunit (CarB) of said enzyme can effectively remove the inhibition effect of UMP. In the present invention, a recombinant strain carrying a gene encoding the CarB (S948F) mutation is obtained by performing a mutation on the carB gene in a chromosome.

A second step of catalysis in the pyrimidine nucleotide synthesis pathway is catalyzing synthesis of carbamoyl aspartate by aspartate carbamyltransferase. Said enzyme consists of a regulatory subunit (PyrI) and a catalytic subunit (PyrB). When the concentration of CTP is high, CTP is combined with PyrI, thereby reducing the activity of the enzyme. If the regulatory subunit encoding the aspartate carbamyltransferase is destroyed, for example, an encoding gene thereof is knocked out, the feedback inhibition effect of the end product CTP on the enzyme is removed (Coudray L 2009, Bioorg Med Chem. 17(22):7680-9).

In the pyrimidine nucleotide synthesis pathway, pyrE encodes orotate phosphoribosyltransferase, to catalyze orotic acid to synthesize orotate monophosphate, and there is a frameshift mutation near a termination codon of an rph gene upstream of the pyrE gene in host bacteria of *Escherichia coli* W3110 (Kaj Frank Jensen 1993, Journal Of Bacteriology, 3401-3407.), causing transcription of some rph genes incapable to stop, thereby affecting expression of downstream pyrE genes and leading to accumulation of orotic acid in the host bacteria. The accumulation of the by-product orotic acid can be effectively reduced to zero by correcting pyrE in a genome, or by overexpression of pyrE under an active promoter such as trc promoter (J. Brosius, M. Erfle, J. Storella Spacing of the −10 and −35 regions in the tac promoter Effect on its in vivo activity, J. Biol. Chem., 260 (1985), 3539-3541), bacteriophage λ pR promoter (Walz, A., Pirrotta, V. Sequence of the PR promoter of phage k. Nature 254, 118-121 (1975)).

In addition, in the pyrimidine nucleotide synthesis, ribose is combined into nucleoside by using phosphoribosylpyrophosphate as a precursor, and phosphoribosylpyrophosphate kinase (Prs) catalyzes a reaction between 5-phosphate ribose and ATP to synthesize phosphoribosylpyrophosphate PRPP.

However, the phosphoribosylpyrophosphate kinase derived from *Escherichia coli* is subject to feedback inhibition imposed by ADP. A mutation, such as from glutamic acid to alanine at positon 128 (D128A) on Prs can effectively remove the feedback inhibition effect of ADP on the Prs (Shimaoka 2007 J Biosci Bioeng 103(3):255-61.).

UMP kinase encoded by a pyrH gene catalyzes phosphorylation of UMP to synthesize uridine diphosphate UDP, but said enzyme is subject to feedback inhibition imposed by its product UDP. Some literature reports that a mutation from aspartic acid to alanine at position 93 (D93A) on said enzyme can effectively remove the corresponding feedback inhibition effect (Meyer P 2008, J Biol Chem. 283(51): 36011-8.).

Beneficial effects: the present invention has the following advantages: compared with the prior art, the present invention provides a recombinant microorganism for producing citicoline and a production method implementing a simple and a high yield of citicoline by means of a biological method using the recombinant microorganism, thereby developing a non-polluting and low-cost citicoline synthesis method, which has the following beneficial effects: during a microbial fermentation process, a certain amount of cytidine triphosphate is accumulated in a cell using glucose and choline, a recombinant microorganism is established by using a genetically manipulated biological material, the microorganism is modified by means of metabolic engineering, the pool of cytidine triphosphate, which is a precursor of citicoline, is enriched in the cell by means of a microbial fermentation method, and finally, citicoline is synthesized and accumulated in a growth medium thereof, effectively implementing large-scale industrial production of citicoline, thereby reducing production costs of citicoline and reducing pollution; therefore, the method is environmentally friendly and has a high promotion and application value.

Figure 1:
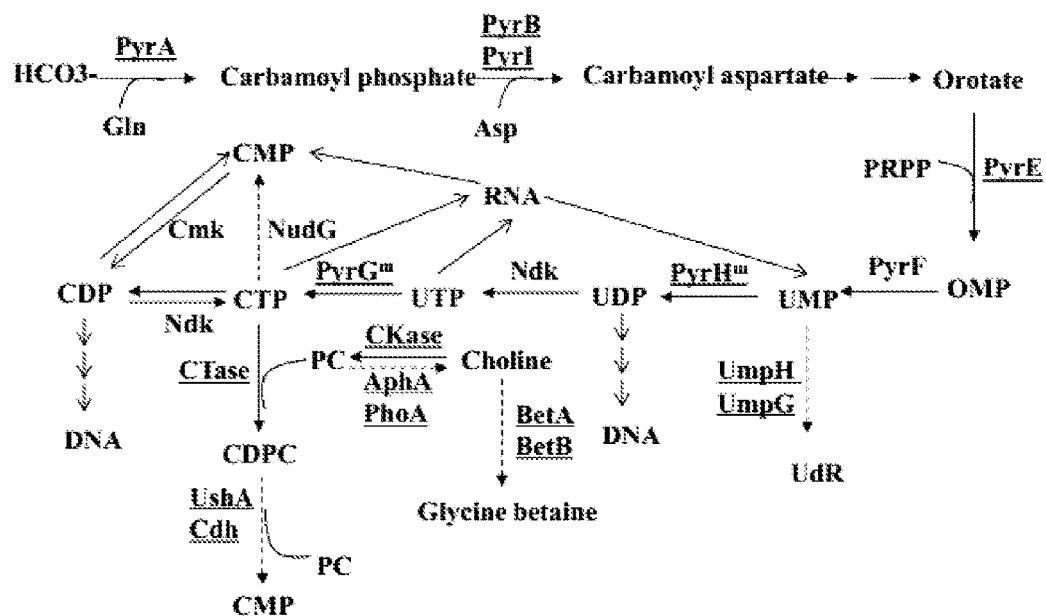
FIG. 1 is a schematic diagram of a metabolic pathway of citicoline in *Escherichia coli*.

Carbamoyl phosphate: Carbamoyl phosphate; carbamoyl aspartate: Carbamoyl aspartate; orotate: Orotate; OMP: Orotate-5'-monophosphate; UMP: Uridine-5'-monophosphate; UDP: Uridine-5'-diphosphate; UTP: Uridine-5'-triphosphate; UdR: Uridine; CdR: Cytidine; CTP: Cytidine-5'-triphosphate; CDP: Cytidine-5'-Diphosphate; CMP: Cytidine-5'-monophosphate; CDPC: Citicoline; PC: Phosphocholine; Choline: Choline; glycine betaine: Glycine betaine; PyrA: Carbamate phosphate synthetase; PyrB/I: Aspartate carbamyltransferase; PyrE: Orotate phosphoribosyltransferase; PyrF: Uridine-5' phosphate decarboxylase; PyrH: Uridine-5'-monophosphate kinase; PyrG: Cytidine triphosphate synthetase; Cmk: Cytidine-5'-monophosphate kinase; CTase: Cytidylyltransferase; CKase: Choline kinase; Ndk: Nucleoside diphosphate kinase; NudG: 5-hydroxy-cytidine triphosphate diphosphatase; UMP: Uridine-5'-monophosphate; UmpG: non-specific nucleotide enzyme/polyphosphatase; UmpH: Uridine 5'-phosphatase; BetA: Choline dehydrogenase; BetB: Betaine aldehyde dehydrogenase; AphA: Acid phosphatase; PhoA: alkaline phosphatase; UshA: UDP-sugar hydrolase; Cdh: Cytidine diphosphate-diacylglycerol pyrophosphatase.

DETAILED DESCRIPTION OF THE PREFERRED EMBODIMENTS

The present invention will be further illustrated below by means of several specific examples, which are only for the purpose of illustration instead of limitation.

Example 1: Method of Knocking Out a Gene in *Escherichia coli*

In the present invention, a Datsenko method was used to knock out a gene in *Escherichia coli* (Datsenko KA 2000, Proc Natl Acad Sci USA, 97(12):6640-6664), and for a corresponding gene knockout primer, reference is made to Baba T. 2006, Mol Syst Biol 2(1), 0008.

Example 2: Method for Verifying a Recombinant Strain Through Shake Flask Fermentation In a fermentation medium for verifying production of citicoline by the recombinant strain through shake flask fermentation, each liter of the medium specifically includes 100 ml of a YC solution, 20 g of glucose, 200 ml of a 5-fold salt solution, 1 ml of a TM2 solution, 10 mg of ferric citrate, 120 mg of anhydrous magnesium sulfate, 111 mg of calcium chloride, and 1 ug of thiamine, with deionized water being used to bring the mixture to a required volume, wherein the 5-fold salt solution consists of 30 g of disodium hydrogen phosphate per liter, 15 g of potassium dihydrogen phosphate per liter, 2.5 g of sodium chloride per liter, and 5.0 g of ammonium chloride per liter, with ionized water being used to bring the mixture to a required volume; and the TM2 solution consists of 2.0 g of zinc chloride tetrahydrate per liter, 2.0 g of calcium chloride hexahydrate per liter, 2.0 g of sodium molybdate dehydrate per liter, 1.9 g of copper sulfate pentahydrate per liter, 0.5 g of boric acid per liter, and 100 ml of hydrochloric acid per liter. A YC solution in the fermentation medium M9 is 100 ml of deionized water; and a YC solution in the fermentation medium MS3.2 consists of 4 g of peptone, 4 g of yeast powder, 10 g of sodium chloride, and 100 ml of deionized water. The above solutions were sterilized at 121° C. for 20-30 minutes.

A shake flask fermentation process is as follows: first, the recombinant strain was inoculated into an LB medium of a certain amount and containing antibiotics (Molecular Cloning: A Laboratory Manual, written by [US] J. Sambrook, translated by Huang Peitang, 2002, 1595), the seeded medium was placed in a 34° C. shaker for overnight incubation at 250 rpm; 100 µl of the above overnight seed culture was taken and transferred to 2 ml LB containing antibiotics, and then was placed in a 34° C. shaker for incubation of 4-6 h at 250 rpm, until an $OD_{600}$ value is about 1.5; after that, the 2 ml of a secondary seed culture was entirely transferred into a shake flask pre-loaded with 18 ml of the fermentation medium, and placed in a 34° C. shaker for incubation at 250 rpm. When $OD_{600}$ value of the culture reached to 1, IPTG was added for a final concentration of 0.1 mM, then choline chloride was added for a final concentration of 4 mM, the incubation continues for about 20 hours, and a fermentation broth was taken for centrifugation detection, wherein for a specific detection method, reference is made to Example 4.

Example 3: Method for Producing Citicoline Through Fermentation Using a Recombinant Strain in a 5 L Fermenter In a fermentation medium for verifying production of citicoline by the recombinant strain through fermentation in a fermenter, each liter of the medium specifically includes 2 g of ammonium sulfate, 8 g of sodium chloride, 2 g of potassium dihydrogen phosphate, 1.65 g of magnesium chloride hexahydrate, 10 g of glucose, 105 mg of calcium chloride, 10 mg of zinc chloride, 1 mL of a TM2 trace element solution, 94 mg of iron citrate, 6 g of peptone, and 6 g of yeast powder, with deionized water being used to bring the mixture to a required volume. The TM2 trace element solution consists of 1.31 g of zinc chloride per liter, 1.01 g of calcium chloride per liter, 1.46 g of ammonium molybdate tetrahydrate per liter, 1.9 g of copper sulfate per liter, 0.5 g of boric acid per liter, and 10 mL of hydrochloric acid per liter, with deionized water being used to bring the mixture to a required volume. A supplementary medium contains 600 g of glucose, 40 g of peptone, and 40 g of yeast powder per liter.

A fermentation process is as follows: first, a seed culture was prepared, a monoclonal culture was picked up from an LB plate and transferred to an LB tube containing antibiotics for overnight incubation at 34° C., the obtained culture was incubated, at an inoculation volume of 1%, into a 500 mL shake flask loaded with 100 mL LB for incubation at 34° C. for 4 hours, until an OD value was 1.5-2; then, the obtained culture was incubated, at an inoculation volume of 5%, into a 5 L fermenter loaded with 1.5 L of fermentation medium MF1.32 for incubation at 37° C., a pH value was adjusted to 6.9 with ammonia water, oxygen dissolution was coupled with a rotation speed to maintain dissolved oxygen at 30%, after 3 hours of fermentation, additional medium was fed at a rate of 8 g/L/h, after 5 hours of fermentation, an OD600 value was 16-25, the temperature was reduced to 32° C., IPTG was added such that a final concentration reaches 0.5 mmol/L for induction, after 10 hours of fermentation, the rotation speed was fixed to 1000 rpm, and when the dissolved oxygen was higher than 40%, coupling feed started, so as to maintain the dissolved oxygen at 30%-45%. Sampling and detection were performed after 27 hours of fermentation, and for a detection method, reference is made to Example 4.

Figure 2:
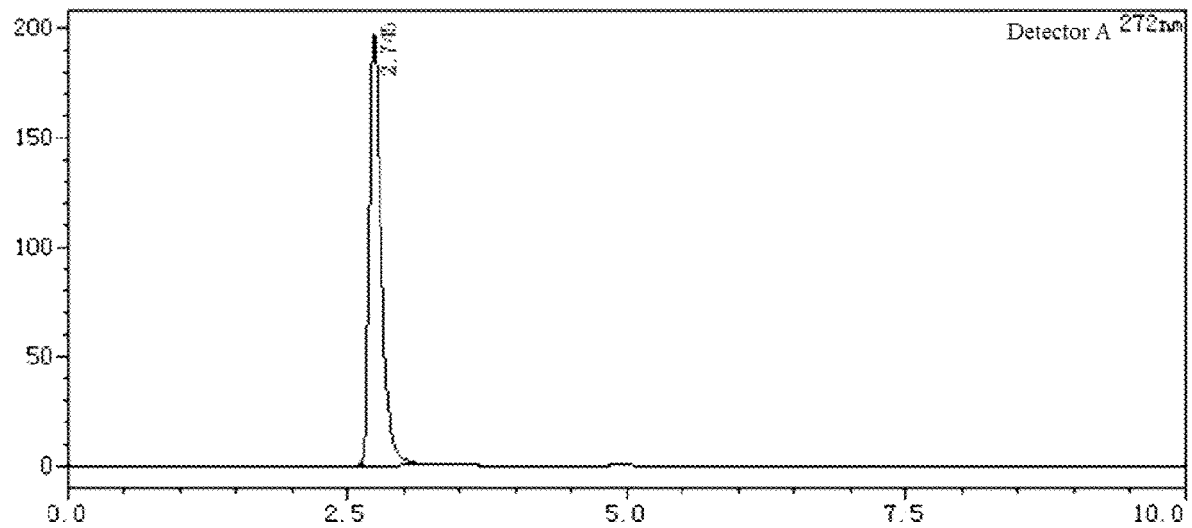
FIG. 2 is an HPLC spectrogram of detection of the citicoline.

Example 4: Measurement of Citicoline and Related by-Products in a Fermentation Broth Through HPLC 200 ul of a fermentation broth was precisely extracted, and added into 800 ul of deionized water, to which 1 ml of absolute ethanol is added, the obtained mixture was subject to vortex shaking for 5 min (at 10,000 rpm), after centrifugation, a supernatant was taken and filtered by a 0.22 um filter membrane, and high-performance liquid chromatography (HPLC) was used for detection, with the following HPLC parameters: Agilent SB C18 4.6*150 mm 5 um is adopted; mobile phases are methanol and 10 mM PBS (pH4.0); the ratio of the mobile phases is as follows: in 0.01-4.00 minutes, the proportion of the methanol is 2%, in 4.00-5.00 minutes, the proportion of the methanol is raised from 2% to 10%, in 4.00-5.00 minutes, the proportion of the methanol is reduced from 10% to 2%, and in 5.10-10.0 minutes, the proportion of the methanol is 2%; a wavelength of 272 nm is detected by an ultraviolet detector; the flow rate of the mobile phase is 0.8 mL/min, the loading amount of the fermentation broth is 5 μL, and the column temperature is 30° C. The CDPC peak time is 2.745 minutes, and the spectrogram is as shown in FIG. 2.

Example 5: Construction of Recombinant Escherichia coli Incapable of Degrading and Utilizing CDPC As shown in FIG. 1, in Escherichia coli, CDPC is catalyzed by UDP-sugar hydrolase (UshA) and CDP-diacylglycerol pyrophosphatase (Cdh) to generate CMP and phosphocholine. In the present invention, Escherichia coli WJ2 (ATCC27325ΔlacI entDT5) was used as an original strain, and encoding genes of UshA and Cdh were knocked out from WJ2 to obtain recombinant bacteria. The ability of these strains to utilize and degrade CDPC was gradually weakened, wherein a recombinant strain HQ24 (WJ2ΔushAΔumpGΔumpHΔpyrIΔcdh) cannot utilize and degrade CDPC in shake flask fermentation. For example, when 2.0 g/L citicoline dicholine is added to the fermentation medium, CDPC residues in WJ2 and WJ3 (WJ2ΔushA) detected after 24 h are 0.15 g/L and 1.02 g/L. [SQ150916 result: 0.3/1.92] indicates that knocking out ushA significantly reduced degradation of CDPC. When 1 g/L citicoline diphosphate is added to the fermentation medium, CDPC residues in HQ19 (WJ2ΔushAΔumpGΔumpH ΔpyrI), HQ24 (HQ19Δcdh), HQ25 (HQ19ΔmazG), and HQ26 (HQ19ΔnudF) detected after 24 h are 0.5 g/L, 1.0 g/L, 0.45 g/L, and 0.46 g/L. It indicates that knocking out cdh could completely eliminate the degradation of CDPC. HQ24/pY022 (pHS01-PCT1-CKI1-pyrE-prs$^{128}$) reached around 17 g/L after fermentation in a fermenter for 26 h.

The recombinant strain HQ24/pY022 strain was deposited on Jun. 26, 2017 at China General Microbiological Culture Collection Center of China Microbe Preservation Management Committee, Address: NO. 3, NO. 1 Courtyard West Beichen Road, Chaoyang District, Institute of Microbiology, Chinese Academy of Sciences, Postcode: 100101, Preservation number: CGMCC No. 14277.

Example 6: Construction of Recombinant Escherichia coli Incapable of Degrading Choline In the present invention, for metabolic production of citicoline by Escherichia coli, exogenously added choline chloride was used as a substrate as the precursor for citicoline synthesis. Under the action of choline dehydrogenase, the substrate choline is oxidized to betaine aldehyde, and then further to glycine betaine under the action of betaine aldehyde dehydrogenase.

In order to prevent degradation of the substrate and the intermediate product, in the present invention, genes betA/B encoding choline dehydrogenase were both knocked out in HQ34 strain.

HQ33 (HQ24ΔpurRΔfhuA::Ptrc-pyrE, carB948) and HQ34 (HQ33ΔbetAB) were respectively used as hosts to express the plasmid pY012. After fermentation in a fermenter for 43 h, the detected yields of CDPC were 18.40 g/L for HQ33/pY012 and 20.87 g/L for HQ34/pY012. It indicates that knocking out choline dehydrogenase could block degradation of the substrate choline chloride, thereby increased the yield of CDPC.

Example 7: Construction of Recombinant Escherichia coli Incapable of Degrading Phosphocholine In the present invention, for production of citicoline, exogenously added choline chloride was used as a substrate, which is catalyzed by choline kinase to generate an intermediate product, i.e., phosphocholine. However, phosphocholine in *Escherichia coli* is prone to hydrolysis to choline by acid phosphatase or alkaline phosphatase present in a cell.

In order to prevent degradation of the intermediate product phosphocholine, in the present invention, coding genes of AphA phoA of were knocked out in HQ35 and HQ36, respectively.

HQ33 (HQ24ΔpurRΔfhuA::Ptrc-pyrE, carB948), HQ35 (HQ33ΔaphA), and HQ36 (HQ33ΔphoA) were used as hosts to express the plasmid pY012. After shake flask fermentation in a fermentation medium, the detected yields of CDPC in above strains were 1.82 g/L, 1.86 g/L, and 1.87 g/L, respectively. It indicates that knocking out phosphatase could reduce or block the degradation of the intermediate product phosphocholine, such that more phosphocholine could be used for product synthesis, thereby increasing the yield of CDPC.

Example 8: Overexpression of Cytidylyltransferase and/or Choline Kinase for Increasing the Yield of CDPC When degradation genes of citicoline and of the substrate choline and the intermediate product phosphocholine thereof are knocked out, the yield of CDPC is very low, indicating insufficient expression of a key intracellular enzyme for catalyzing choline to generate CDPC. In order to increase the yield of CDPC in a cell, in the present invention, CTase and CKase in the CDPC synthesis process were expressed appropriately. When plasmids expressing different genes encoding CTase and/or CKase were transformed into *Escherichia coli* expression hosts, the yield of CDPC was increased in varying degrees. For example, when plasmids pHS01 (pCL1920 PLac::Ptrc, see LS9 patent US20130029395A1), pY008 (pHS01-PCT1-CKI1), and pY012 (pHS01-PCT1-CKI1-licC) are expressed in HQ33, after shake flask fermentation culture for 24 hours, the yields of CDPC are respectively 0 g/L, 1.44 g/L, and 1.55 g/L.

Example 9: Overexpression of Choline Transporter Protein for Increasing the Yield of CDPC BetT is a choline transporter protein driven by hydrogen ions and belongs to the family of betaine choline transporter BCCT. Said protein is expressed in an aerobic condition and induced by osmotic pressure. High osmotic pressure can enhance transcription of BetT, and addition of choline can further enhance the transcription. In order to obtain more CDPC, choline chloride needs to be supplied more quickly. In order to increase entering of the choline chloride into a cell, which is a rate-limiting step, BetT was overexpressed, so as to obtain more transporter protein in a case where the osmotic pressure was not increased. HQ33 was used as a host to respectively express pY012 and pY012-betT, and after shake flask fermentation in a fermentation medium for 24 h, the detected yield of CDPC in the former case was 2.36 times of that in the latter case. It indicates that overexpression of betT could significantly increase the yield of CDPC.

Example 10: Knocking Out of an Encoding Gene of UMP Degrading Enzyme for Increasing the Yield of CDPC Uridine monophosphate UMP is an intermediate product of the pyrimidine synthesis pathway, can generate uridine diphosphate UDP under the action of uridine 5'-monophosphatase through a replenishment pathway, and can further be degraded into uridine under the action of 5'-nucleotidase. In order to obtain a larger amount of the CDPC product, in the present invention, encoding genes umpG and umpH of the 5'-nucleotidase were knocked out in HQ18. WJ3 and HQ18 (WJ3ΔumpGΔumpH) were used as hosts to transform the plasmid pY022 (pY008-pyrE-prs$^{128}$), and after shake flask fermentation in a fermentation medium for 24 h, the detected yields of CDPC were 1.9 g/L and 1.92 g/L, respectively. For a strain HQ18/pY022, a yield could reach 8.93 g/L after fermentation in a 5 liter fermenter for 26 h.

Example 11: Overexpression of PyrE for Increasing the Yield of CDPC

Overexpression of the pyrE gene in a plasmid and a genome could remove defect caused by a frameshift mutation of the upstream rph gene, thereby increase the yield of CDPC. For example, when HQ04 (W3110 (ΔdeoA Δung ΔpurR ΔushA ΔbetABI, Ptrc-betT)) is used as a host to express pY008 and pY009 (pY008-pyrE), respectively, and after shake flask fermentation in a fermentation medium, the yield of CDPC is increased from 0.67 g/L to 0.80 g/L. It indicates that the overexpression of pyrE could increase the yield of citicoline.

Example 12: Overexpression of Prs128 for Increasing the Yield of CDPC

In the pyrimidine synthesis pathway of *Escherichia coli*, under the action of orotate phosphoribosyltransferase (PyrE), phosphate groups in phosphoribosylpyrophosphate (PRPP) are transferred to orotate, thereby generating orotate monophosphate (OMP). PRPP insufficiency may form a rate-limiting step in the pyrimidine synthesis pathway, resulting in a relatively low yield of citicoline and accumulation of an orotic acid by-product. Phosphoribosylpyrophosphate kinase (Prs) catalyzes a reaction between 5-phosphate ribose and ATP to synthesize PRPP. However, Prs is subject to feedback inhibition imposed by ADP and others, and a mutation from aspartic acid to alanine at position 128 in Prs for obtaining Prs128 could remove the feedback inhibition. For example, when WJ3 is used as a host to respectively express pY017 (pY009-prs) and pY022 (pY009-prs$^{128}$), and after shake flask fermentation in a fermentation medium, the yield of CDPC is increased from 1.80 g/L to 1.96 g/L.

Example 13: Knocking Out of an Encoding Gene of PyrI for Increasing the Yield of CDPC A second step of catalysis in the pyrimidine nucleotide synthesis pathway is catalyzing synthesis of carbamoyl aspartate by aspartate carbamyltransferase. Said enzyme consists of a regulatory subunit (PyrI) and a catalytic subunit (PyrB). When the concentration of CTP is high, CTP is combined with PyrI, thereby reducing the activity of the enzyme. In the present invention, the encoding gene of PyrI was knocked out, so as to remove the feedback inhibition effect of the end product CTP on the enzyme. For example, when pY022 is expressed in HQ18 and HQ19 (HQ18ΔpyrI), which are used as hosts, and after shake flask fermentation in a fermentation medium, the yield of CDPC is increased from 1.74 g/L in HQ18 to 1.92 g/L in HQ19. It indicates that knocking out the gene of pyrI could remove the feedback inhibition on aspartate carbamyltransferase imposed by CTP, thereby accelerating synthesis of the pyrimidine synthesis pathway and increasing the yield of CDPC.

Example 14: Knocking Out of Encoding Genes of Repressor Proteins PurR and ArgR for Increasing the Yield of CDPC A first step of the pyrimidine nucleotide synthesis pathway is catalyzing synthesis of carbamoyl phosphate by carbamoyl phosphate synthetase. The encoding gene carAB of said enzyme is subject to a feedback repression effect of metabolic end products such as purine, pyrimidine, and arginine. In addition, purine nucleotide is inhibited by repressor protein encoded by the purR gene, and arginine is inhibited by repressor protein encoded by the argR gene. In the present invention, transcription inhibition to carAB was removed by knocking out purR and argR, thereby accelerating synthesis of carbamoyl phosphate. For example, when pY022 is respectively expressed in HQ19, HQ22 (HQ19ΔpurR), HQ20 (HQ18ΔpurR) and HQ21 (HQ20ΔargR), and after shake flask fermentation in the fermentation medium MS3.2, the yields of CDPC are 1.25 g/L and 1.54 g/L; and 1.15 g/L and 1.34 g/L, respectively. It indicates that knocking out purR or argR gene could remove the feedback repression to carAB, thereby promoting the synthesis of the pyrimidine pathway and increasing the yield of CDPC.

Only some of the embodiments of the present invention are described above. It should be noted that those skilled in the art could make some improvements without departing from the principle of the present invention, and these improvements shall also fall into the protection scope of the present invention.

The invention claimed is:

1. A genetically modified *Escherichia coli* for producing citicoline comprising the following modifications:
    a. enzymes involved in reuse of citicoline, or choline, or phosphocholine being disrupted, wherein the enzymes comprise cytidine-5'-diphosphoinositol hydrolase, cytidine-5'-diphosphate-diacylglycerol pyrophosphatase, choline dehydrogenase, alkaline phosphatase or acid phosphatase;
    b. choline kinase for catalyzing choline chloride to generate phosphocholine being overexpressed, wherein the choline kinase comprises CKI1 or EKI1 obtained from *Saccharomyces cerevisiae*, or LicC obtained from *Streptococcus*;
    c. cytidylyltransferase for catalyzing phosphocholine to generate citicoline being overexpressed, wherein the cytidylyltransferase comprises PCT1, CDS1, or ECT1 obtained from *Saccharomyces cerevisiae*; or CdsA, IspD, MocA, KdsB, or Cca obtained from *Escherichia coli*; or LicC obtained from *Streptococcus*; or CD36_40620 obtained from *Candida dubliniensis*;
    d. choline transporter protein, for transporting choline chloride into a cell being overexpressed, wherein the choline transporter protein comprises BetT obtained from *Escherichia coli*; and
    e. uridine-5'-monophosphate phosphorylase for degrading uridine-5'-monophosphate into uridine is disrupted; and the uridine-5'-monophosphate phosphorylase comprises UmpH, UmpG, PhoA, AphA, or YjjG.

2. The genetically modified *Escherichia coli* of claim 1 comprising further modifying the *Escherichia coli* by disrupting a repressor protein gene by means of one or more of the following processes:
    a. disrupting one or more of the genes selected from purR, pepA, and argR;
    b. comprising the S948F mutation in carbamoyl phosphate synthetase subunit (CarB);
    c. disrupting the pyrI subunit of aspartate carbamyltransferase;
    d. comprising the D128A mutation in phosphoribosylpyrophosphate kinase; and
    e. comprising the D160E, E162A or E168K mutation, or combinations thereof in cytidine triphosphate synthetase (PyrG).

3. A method for producing citicoline by culturing the genetically modified *Escherichia coli* according to claim 1 with choline chloride added as a substrate.

\* \* \* \* \*